United States Patent
Leonard et al.

(10) Patent No.: US 8,449,925 B2
(45) Date of Patent: *May 28, 2013

(54) METHOD AND USE OF COLD-PRESSED BOTANIC SEED OILS FOR LOWERING BLOOD PRESSURE AND LDL CHOLESTEROL

(75) Inventors: Arnold Leonard, Minneapolis, MN (US); Daniel Saltzman, Mendota Heights, MN (US); Mark J. Mueller, Spooner, WI (US)

(73) Assignee: Botanic Oil Innovations, Inc., Spooner, WI (US)

( * ) Notice: Subject to any disclaimer, the term of this patent is extended or adjusted under 35 U.S.C. 154(b) by 264 days.

This patent is subject to a terminal disclaimer.

(21) Appl. No.: 12/166,528

(22) Filed: Jul. 2, 2008

(65) Prior Publication Data

US 2008/0260645 A1    Oct. 23, 2008

Related U.S. Application Data

(63) Continuation-in-part of application No. 10/834,587, filed on Apr. 29, 2004, and a continuation-in-part of application No. 11/220,473, filed on Sep. 7, 2005, and a continuation-in-part of application No. 11/421,926, filed on Jun. 2, 2006, and a continuation-in-part of application No. 11/787,796, filed on Apr. 18, 2007.

(60) Provisional application No. 60/792,763, filed on Apr. 18, 2006.

(51) Int. Cl.
*A61K 36/00* (2006.01)

(52) U.S. Cl.
USPC .......................................... 424/725

(58) Field of Classification Search
None
See application file for complete search history.

(56) References Cited

U.S. PATENT DOCUMENTS

2008/0107758 A1 * 5/2008 Crutchfield, III ............. 424/732

FOREIGN PATENT DOCUMENTS

WO    WO 00/32211    *    6/2000

OTHER PUBLICATIONS

Parker et al (Journal of Food Science (68(4): 1240-1243, 2003).*
Teres et al. Oleic Acid Content is Responsible for the Reduction in Blood Pressure induced by Olive Oil. PNAS. Sep. 16, 2008. vol. 105, No. 37. pp. 13811-13816.*
Harper et al. Flaxseed oil Supplementation Does Not Affect Plasma Lipoprotein Concentration or Particle Size in Human Subjects. The Journal of Nutrition. 2006. pp. 2844-2848.*
West. Inhibitory Effect of Selected Spice and Fruit Seed Extracts on Lipid Oxidation in Fish Oil and Their Radical Scavenging and Antimicrobial Properties. 2006. Pages.*
Anonymous. Antioxidant-rich Wunderbar. Functional Foods & Nutraceuticals; Jan. 2006, Career and Technical Education. p. 48.*
Botanic Oil Innovations. Black Cumin Seed Nutri-Powder Flour™. Fall 2005. pp. 1-2.*
The Herbal Encyclopedia. Retrieved from the Interent. Retrieved on Apr. 21, 2011. Webarchive date Feb. 10, 2003. <http://classic-web.archive.org/web/20030210135948/http://www.naturalark.com/herbcomb.html>. pp. 1-9.*

* cited by examiner

*Primary Examiner* — Patricia Leith
(74) *Attorney, Agent, or Firm* — Gerald E. Helget; Nelson R. Capes; Briggs and Morgan, P.A.

(57) ABSTRACT

A method of lowering diastolic blood pressure and LDL cholesterol in a human subject. The method consists of the steps of: (a) administering to the human subject a mixture of cold-pressed botanic seed oils; (b) administering to the human subject the mixture of cold-pressed botanic seed oils and a mixture of botanic seed flours; and (c) lowering the human subject's diastolic blood pressure and LDL cholesterol.

A method of measurement of the synergistic effect of cold-pressed botanic seed oils and botanic seed flours in lowering diastolic blood pressure and LDL cholesterol in a human subject. The method consists of the steps of: a) administering to the human subject a mixture of cold-pressed botanic seed oils; b) administering to the human subject a mixture of botanic seed flours; and c) measuring the human subject's diastolic blood pressure and LDL cholesterol.

A composition of matter exhibiting diastolic blood pressure lowering activity and LDL cholesterol lowering activity in a human subject. The composition of matter consists of a mixture of cold-pressed botanic seed oils and a mixture of botanic seed flours.

4 Claims, No Drawings

METHOD AND USE OF COLD-PRESSED BOTANIC SEED OILS FOR LOWERING BLOOD PRESSURE AND LDL CHOLESTEROL

CROSS-REFERENCE TO RELATED APPLICATIONS

This patent application is a continuation-in-part of U.S. patent application Ser. No. 10/834,587, filed Apr. 29, 2004; and a continuation-in-part of U.S. patent application Ser. No. 11/220,473, filed Sep. 7, 2005; and a continuation-in-part of U.S. patent application Ser. No. 11/421,926, filed Jun. 2, 2006 and a continuation-in-part of U.S. patent application Ser. No. 11/787,796, filed Apr. 18, 2007, which claims priority under 35 USC 120 to U.S. Provisional Patent Application No. 60/792,763, filed Apr. 18, 2006.

FIELD OF THE INVENTION

This invention relates to a method and composition of matter for lowering diastolic blood pressure and LDL cholesterol in human beings using cold-pressed botanic seed oils and botanic seed flours.

BACKGROUND OF THE INVENTION

Public health in the United States is characterized by highly prevalent chronic disease conditions. More than 90 million Americans live with chronic illnesses which result in 70% of the deaths in the United States each year. The medical care costs of people with chronic diseases account for more than 75% of the nation's $1.4 trillion medical care costs. Many of these conditions are linked to systemic stress and production of free radicals, reduced antioxidant defense, and attenuated nitric oxide synthase (NOS) activity.

Free radicals (oxidation) are highly charged molecules with open negative charges which are involved with cell and tissue damaging biochemical reactions. Of particular interest are lipid peroxidation reactions resulting in an increase in LDL cholesterol as well as a reduction of the compliance of the arterial walls by increased cross-linking between cells. Previous work by Niki et al. has shown that various antioxidants with different functions inhibit lipid peroxidation and the deleterious effects caused by the lipid peroxidation products. (Niki E, Yoshida Y, Saito Y et al. "Lipid peroxidation: mechanisms, inhibition, and biological effects." Biochem Biophys Res Commun. 2005 Dec. 9; 338(1):668-76.) Work performed by Leonard et al. demonstrated in laboratory procedures that black cumin oil has strong free radical quenching activity and has significant inhibitory effect on LDL oxidation. (Leonard, A S, Saltzman, D A, Mueller, M: Creation of Super-Potent Antioxidant Values Through Synergy of Cold-Pressed Botanic Oils for Therapeutic Purposes. Naturopathy Digest Vol 1, No 7, July 2006.) [hereinafter "Leonard"]

The biological roles of lipid peroxidation products have recently received a great deal of attention, but its clinical significance must be demonstrated in future studies. Animal studies on antioxidants have demonstrated that treatment initiated to reduce oxidative stress prevents the age-associated development of high blood pressure in genetically hypertensive rats. (Nabha L, Garbem J C, Buller C L et al. "Vascular oxidative stress precedes high blood pressure in spontaneously hypertensive rats." Clin Exp Hypertens. 2005 January; 27(1):71-82.)

Clinical trials with humans focusing on antioxidants and cardiovascular disease have in the past been unsuccessful due to the dose-dependent effects of antioxidants, for example studies on vitamin E. However, in animal trials, a correlation was found between dosage of antioxidant consumption and the effect of reduction of cholesterol for hyperlipidemic mice and rabbits. (Weinberg P D et al. "Analysis of the variable effect of dietary vitamin E supplements on experimental atherosclerosis." J Plant Physio. 2005 July; 162(7): 823-33.)

The antioxidant supplement Immuno-Viva™, investigated in human subjects in this patent application is a pure blend of black raspberry and black cumin seed oils using a proprietary Nature FRESH-Cold Press™ processing technology. The Immune Lift™ antioxidant supplement is a blend of de-fatted black cumin seed flour and de-fatted black raspberry seed flour. Both products are manufactured by Botanic Oil Innovations, Inc., Spooner, Wis. The proprietary process is carried out in an oxygen deprived nitrogen/carbon dioxide atmosphere which optimizes nutrient yield. The process does not involve solvents, bleaching agents or high temperatures. The products contain high levels of alpha, gamma and beta tocopherols, as well as in gamma tocotrienols. Main components of the products are—saturated, mono-unsaturated, poly-unsaturated fatty acids and carbohydrate. The omega 3:6 ratio equals 2:5. (Leonard)

Preliminary animal studies have evaluated the effects of black raspberry seed oil (Botanic Oil Innovations, Inc.) on splenic lymphocyte populations in mice. The study showed that mice fed standard meals with 10% oil added showed significantly elevated levels of natural killer cells (NK) and cytotoxic T lymphocyte cells (CD 8). Both NK and CD 8 are believed to enable the body to better fight the damage caused by free radicals and to enhance the body's ability to fight disease and cancer. (Leonard)

Further preliminary pilot tests have evaluated a possible synergistic effect of Immuno-Viva™ oil and an attenuated *Salmonella Typhimurium* that synthesizes interleukin 2 (IL-2). It was shown that the IL-2 reduced hepatic metastases by 58% in mice, and an additional 30% reduction in metastases was found including the oil. (Saltzman D A, Leonard A S: Studies of the Immune Enhancement and Anti-Tumor Properties of Highly Potent Antioxidant Oils in Conjunction with Attenuated Salmonella Typhimurium Containing the Gene for Interleukin-2. University of Minnesota. 2006).

SUMMARY OF THE INVENTION

In one aspect, the present invention is a method of lowering diastolic blood pressure and LDL cholesterol in a human subject comprising the steps of: (a) administering to the human subject a mixture of cold-pressed botanic seed oils; (b) administering to the human subject the mixture of cold-pressed botanic seed oils and a mixture of botanic seed flours; and (c) lowering the human subject's diastolic blood pressure and LDL cholesterol.

In another aspect, the present invention is a method of measurement of the synergistic effect of cold-pressed botanic seed oils and botanic seed flours in lowering diastolic blood pressure and LDL cholesterol in a human subject, comprising the steps of: a) administering to the human subject a mixture of cold-pressed botanic seed oils; b) administering to the human subject a mixture of botanic seed flours; and c) measuring the human subject's diastolic blood pressure and LDL cholesterol.

In another aspect, the present invention is a composition of matter exhibiting diastolic blood pressure lowering activity and LDL cholesterol lowering activity in a human subject.

The composition of matter consists of a mixture of cold-pressed botanic seed oils and a mixture of botanic seed flours.

BRIEF DESCRIPTION OF DRAWINGS

None.

DETAILED DESCRIPTION OF THE PREFERRED EMBODIMENT

Population and Sample Selection

The Minneapolis-St Paul area population was over 2.8 million in the 2000 census. The gender distribution is 51% female and 49% male, and ethnicity distributions were roughly: White 85%, African American 6%, American Indian 0.7%, Asian 4.5%, Hispanic 4%, Pacific Islander 0.05%, Other 4%.

Primary population sources were employees and former study participants at the Berman Center for Outcomes and Clinical Research. Additional sampling was sought among relatives and friends of the primary enrollments.

Thirty potential participants were screened. Thirty participants were eligible and initiated the study. One participant never started the procedure and returned the study oil unused. Two participants discontinued the study after one month for medical or personal reasons. Thus, twenty nine participants completed month one of the study and twenty seven participants completed the entire study.

FIG. 1 is a general flowchart of the method of the present invention.

Protocol

Day 0 the prospective participant visited the Berman Center for Outcomes and Clinical Research after an overnight fast of at least 10 hours and not more than 12 hours.

The investigator contacted the participant by telephone to verify adherence to fasting prior to arriving at the clinic.

Baseline Measurements and Procedures

Informed Consent and HIPAA forms, approved by the Hennepin County Medical Center and University of Minnesota Institutional Review Boards, were reviewed and signed and medical history and current medication log was obtained. The following measurements were performed:

Body weight using a calibrated lever scale
Body height using a statiometer
Blood Pressures and pulse rate using a digital blood pressure monitor (HEM-907, Omron, Vernon Hills, Ill.) (Three consecutive measurements after a five minutes rest in the sitting position).

A blood sample was taken and analyzed later for ALT, AST, creatinine, Complete Blood Count (CBC), bilirubin, C-reactive protein, lipids, and lymphocytes using analytical methods described below, at the Hennepin Faculty Associates (HFA) Laboratory and the University of Minnesota. A urine sample was obtained and analyzed for malondialdehyde (MDA) at the Berman Center. The participant received the Immuno-Viva™ product and instructions.

Days 1-29 Participants were instructed to consume 1.5 teaspoons (7.5 g) of the mixture of oils twice a day in combination with 8 ounces (2.5 dl) of water. No other dietary or life style changes were prescribed.

Day 30 Participants were seen at the Berman Center after overnight fasting and it was important that no oil had been consumed 10-12 hours prior to arrival at the clinic. The procedure from day 0 was repeated. At this visit the participant was also given the Immune Lift™ product and instructions.

Days 30-59 Participants continued the daily routine, consuming 1.5 tsp of Immuno-Viva™ twice a day in combination with water. However, two tablets of Immune Lift™ were added in the morning only. No other dietary or life style changes were recommended.

Day 60 Participants attended a clinic visit at the Berman Center after fasting overnight and no oil or tablets had been consumed 10-12 hours prior to arrival at the clinic. The procedures from day 0 (baseline) were repeated. The measures done at each visit are detailed in the grid below.

Table 1 is a measurement grid of the measurements taken at various points in the study.

TABLE 1

|  | Day 0 Baseline Visit | Day 30 Follow-up Visit | Day 60 Close-out Visit |
| --- | --- | --- | --- |
| Body Height | X |  |  |
| Body Weight | x | x | x |
| Blood Pressure | x | x | x |
| Blood Sample | X | X | X |
| CBC w/differential | x | x | x |
| Lymphocyte | x | x | x |
| ALT | x | x | x |
| AST | x | x | x |
| Creatinine | x | x | x |
| Total Bilirubin | x | x | x |
| Cardiac C-reactive protein | x | x | x |
| Lipid Profile | x | x | x |
| Urine Sample | X | X | X |
| Malondialdehyde (urine) | x | x | x |

Table 2 is a listing of the analytical methods used for various measurements.

TABLE 2

| CBC w/differential | Flow Cytometry |
| --- | --- |
| Lymphocyte | Multi-color Immunofluorescence and Flow Cytometry |
| ALT (SGPT) | Rate reflectance spectrophotometry |
| AST (SGOT) | Rate reflectance spectrophotometry |
| Creatinine | Rate reflectance spectrophotometry |
| Malondialdehyde | Colorimetric Assay (Visual reading) |
| Bilirubin | Spectrophotometry |
| Cardiac C-reactive Protein | Enhanced Turbometric Immuno Assay |
| Lipid Profile | Colorimetric rate reflectance spectrophotometry |

Statistics

The endpoint data obtained on days 0, 30, 60 was examined for normal distribution in order to determine the appropriate statistic to apply. The data was interpreted using ANOVA statistics for continuous data, and significant differences were sought at the alpha=0.05 level with a power of 80%.

The detectable differences of the variables were calculated according to the formula:

$$D^2 = (z_{a/2} + z_b)^2 * s^2 * (1/n_1 + 1/n_2) * DEFF$$

Where D is the detectable difference, $z_{a/2}$ and $z_b$ are the critical points on the Gaussian distributions for the type 1 and 2 error rates, s is the estimated standard deviation of the variable, $n_1$ and $n_2$ are the sample sizes at days 30 and 60, and DEFF is the variance inflation factor for the particular variable.

Verification of Safety

A primary outcome was to look at the safety of Immuno-Viva™ and Immune Lift™. Table 3 shows the proportions of individuals who were in the normal ranges for the safety outcomes. The individual who had out of normal range values for ALT and AST at baseline was the same individual who had out of normal range values at day 30 and day 60. Creatinine was found to be statistically significantly higher than baseline values at day 30 and then normalized to baseline values by day 60. Table 3 shows none of the participants went over the upper boundary of normal for creatinine. Therefore, we conclude that Immuno-Viva™ and/or Immune Lift™ are safe dietary supplements for healthy individuals.

TABLE 3

Proportions of (Normal values/Total Sample)

|  | Baseline | Day 30 | Day 60 |
|---|---|---|---|
| ALT | 28/29 | 28/29 | 26/27 |
| AST | 28/29 | 28/29 | 26/27 |

TABLE 3-continued

Proportions of (Normal values/Total Sample)

|  | Baseline | Day 30 | Day 60 |
|---|---|---|---|
| Creatinine | 29/29 | 29/29 | 27/27 |
| Bilirubin | 28/29 | 29/29 | 26/27 |
| Eosinophils | 27/29 | 27/29 | 26/27 |
|  | 13/15 ≧ 45 | 13/15 ≧ 45 | 13/14 ≧ 45 |

Secondary outcomes were collected to look at trends for future research studies. Repeated measure ANOVA was performed on each variable for the entire cohort as well as a separate repeated measure ANOVA only on those individuals at or above the age of 45 (n=14). Tables 4, 5, 6, and 7 summarize the results obtained from these analyses.

TABLE 4

The Entire Cohort
Characteristics, safety, CRP, and lipid profile data on days 0, 30 and 60.

|  | Group means ||| Group differences ||| |
|---|---|---|---|---|---|---|---|
|  | D0 N = 29 | D30 N = 29 | D60 N = 27 | D30 − D0 | D60 − D30 | D60 − D0 | F-value P-value |
| BMI (kg/m$^2$) | 28.3 (4.7) | 28.2 (4.6) | 28.2 (4.7) | −0.1 | 0 | −0.1 | 0.49 .616 |
| BPsystolic (mmHg) | 110.1 (13.3) | 106.9 (12.8) | 108.8 (15.0) | −3.2 | 1.9 | −1.3 | 1.71 0.192 |
| BPdiastolic (mmHg) | 70.6 (10.9) | 67.0 (9.4) | 69.3 (8.9) | −3.6 | 2.3 | −1.3 | 4.03 0.024 |
| Bilirubin (mg/dl) | 0.9 (.23) | 0.8 (.24) | 0.9 (.22) | −0.1 | 0.1 | 0 | 0.79 0.459 |
| ALT (IU/l) | 23.8 (20.8) | 23.1 (20.1) | 25.9 (34.2) | −0.7 | 2.8 | 2.1 | 0.74 0.484 |
| AST (IU/l) | 25.3 (15.6) | 24.3 (12.7) | 25.6 (19.6) | −1 | 1.3 | 0.3 | 0.56 0.573 |
| Creatinine (mg/dl) | 0.9 (.14) | 1.0 (.17) | 0.9 (.15) | 0.1 | −0.1 | 0 | 4.26 0.019 |
| Triglyceride (mg/dl) | 92.4 (46.1) | 88.9 (39.0) | 98.6 (49.3) | −3.5 | 9.7 | 6.2 | 1.75 0.186 |
| Cholesterol (mg/dl) | 187.0 (34.5) | 182.2 (31.1) | 183.1 (27.8) | −4.8 | 0.9 | −3.9 | 1.11 0.337 |
| HDL (mg/dl) | 55.0 (20.8) | 53.7 (20.1) | 54.6 (20.5) | −1.3 | 0.9 | −0.4 | 0.75 0.479 |
| LDL (mg/dl) | 113.6 (28.7) | 111.1 (28.1) | 108.6 (28.4) | −2.5 | −2.5 | −5 | 1.63 0.206 |
| VLDL (mg/dl) | 18.5 (9.3) | 17.7 (7.7) | 19.8 (9.9) | −0.8 | 2.1 | 0.3 | 1.99 0.147 |
| CRP | 2.5 (2.7) | 2.9 (2.7) | 2.5 (3.3) | 0.4 | −0.4 | 0 | 1.07 0.350 |

Legend:
D0: Baseline values (means with (standard deviations)) prior to the intervention.
D30: Values obtained after 1 month of Immuno Viva intervention.
D60: Values obtained after 1 month of Immuno Viva + Immune Lift intervention.
Statistically significant values are in bold type

TABLE 5

Entire Cohort
Hematology, immuno chemistry and urine data on days 0, 30 and 60.

|  | Group means ||| Group differences ||| |
|---|---|---|---|---|---|---|---|
|  | D0 N = 29 | D30 N = 29 | D60 N = 27 | D30 − D0 | D60 − D30 | D60 − D0 | F-value P-value |
| WBC (k/cmm) | 5.9 (1.6) | 5.9 (1.3) | 5.6 (1.4) | 0 | −0.3 | −0.3 | 1.23 0.302 |
| Neutrophil (%) | 60.6 (7.2) | 60.4 (7.7) | 58.4 (7.3) | −0.2 | −2 | −2.2 | 2.58 0.085 |
| Lymphocyte (%) | 27.5 (7.1) | 27.8 (7.6) | 29.4 (7.0) | 0.3 | 1.6 | 1.9 | 2.37 0.103 |

TABLE 5-continued

Entire Cohort
Hematology, immuno chemistry and urine data on days 0, 30 and 60.

| | Group means | | | Group differences | | | F-value P-value |
|---|---|---|---|---|---|---|---|
| | D0 N = 29 | D30 N = 29 | D60 N = 27 | D30 − D0 | D60 − D30 | D60 − D0 | |
| Monocyte | 8.5 | 8.6 | 8.5 | 0.1 | −0.1 | 0 | 0.15 |
| (%) | (3.0) | (2.2) | (2.2) | | | | 0.860 |
| Eosinophil | 2.7 | 2.6 | 3.2 | −.01 | 0.6 | 0.5 | 5.35 |
| (%) | (1.4) | (1.4) | (1.8) | | | | 0.008 |
| Basophil | 0.6 | 0.6 | 0.50 | 0 | −0.1 | −0.1 | 1.80 |
| (%) | (.32) | (.31) | (.36) | | | | 0.176 |
| CD3 | 73.5 | 74.0 | 73.6 | 0.5 | −0.4 | 0.1 | 0.74 |
| | (5.7) | (5.5) | (5.4) | | | | 0.482 |
| CD4 | 50.7 | 51.2 | 50.5 | 0.5 | −0.7 | −0.2 | 0.76 |
| | (6.9) | (7.2) | (7.7) | | | | 0.471 |
| CD8 | 21.1 | 21.8 | 21.6 | 0.7 | −0.2 | 0.5 | 1.11 |
| | (6.1) | (5.9) | (5.9) | | | | 0.336 |
| CD19 | 14.7 | 14.8 | 15.0 | 0.1 | 0.2 | 0.3 | 0.35 |
| | (4.1) | (3.9) | (3.9) | | | | 0.708 |
| NK | 10.6 | 10.0 | 10.6 | −0.6 | 0.6 | 0 | 0.59 |
| | (5.2) | (4.8) | (4.3) | | | | 0.559 |
| CD4:CD8 | 2.6 | 2.6 | 2.6 | 0 | 0 | 0 | 0.42 |
| | (1.0) | (1.1) | (1.1) | | | | 0.656 |
| Malonyldiald. | 2.6 | 2.9 | 3.0 | 0.3 | −0.1 | 0.4 | 0.64 |
| | (1.5) | (1.3) | (1.3) | | | | 0.531 |
| CD3absol | 241.2 | 251.8 | 253.7 | 10.6 | 1.9 | 12.5 | 0.64 |
| | (144) | (159) | (139) | | | | 0.529 |

Legend:
D0: Baseline values (means with (standard deviations)) prior to the intervention.
D30: Values obtained after 1 month of Immuno Viva intervention.
D60: Values obtained after 1 month of Immuno Viva + Immune Lift intervention.
WBC: White Blood Cell Count
NK: Natural Killer Cell
Statistically significant values are in bold type

TABLE 6

Sub-group 45 and older
Characteristics, safety, CRP, and lipid profile data on days 0, 30 and 60.

| | Group means | | | Group differences | | | F-value P-value |
|---|---|---|---|---|---|---|---|
| | D0 N = 14 | D30 N = 14 | D60 N = 14 | D30 − D0 | D60 − D30 | D60 − D0 | |
| BMI | 28.7 | 28.6 | 28.6 | −0.1 | 0 | −0.1 | 0.23 |
| (kg/m$^2$) | (5.2) | (5.1) | (5.0) | | | | .794 |
| BPsystolic (mmHg) | 114.9 | 111.9 | 113.5 | −3 | 1.6 | −1.4 | 0.59 |
| | (13.2) | (13.3) | (16.7) | | | | 0.559 |
| BPdiastolic | 74.2 | 71.6 | 73.2 | −2.6 | 1.6 | −1 | 2.06 |
| (mmHg) | (11.0) | (9.6) | (8.8) | | | | 0.147 |
| Bilirubin | 0.91 | 0.85 | 0.89 | −0.06 | 0.04 | −.02 | 0.36 |
| (mg/dl) | (.21) | (.20) | (.18) | | | | 0.699 |
| ALT | 28.1 | 28.8 | 33.1 | 0.7 | 4.3 | 5 | 0.77 |
| (IU/l) | (27.9) | (26.4) | (46.3) | | | | 0.474 |
| AST | 29.4 | 29.1 | 30.4 | −0.3 | 1.3 | 1 | 0.16 |
| (IU/l) | (20.8) | (16.1) | (26.9) | | | | 0.852 |
| Creatinine | 0.9 | 1.0 | 0.9 | 0.1 | −0.1 | 0 | 2.10 |
| (mg/dl) | (.17) | (.21) | (.17) | | | | 0.142 |
| Triglyceride | 104.1 | 92.3 | 106.6 | −11.8 | 14.3 | 2.5 | 1.53 |
| (mg/dl) | (52.7) | (40.7) | (57.9) | | | | 0.235 |
| Cholesterol | 201.4 | 191.5 | 191.4 | −10.1 | −0.1 | −10 | 2.22 |
| (mg/dl) | (32.2) | (28.1) | (27.2) | | | | 0.129 |
| HDL | 57.6 | 55.3 | 58.2 | −2.3 | 2.9 | 0.6 | 1.78 |
| (mg/dl) | (22.5) | (20.7) | (24.2) | | | | 0.188 |
| LDL | 123.0 | 117.8 | 111.8 | −5.2 | −6 | −11.2 | 3.51 |
| (mg/dl) | (28.4) | (26.2) | (30.3) | | | | 0.045 |
| VLDL | 20.9 | 18.4 | 21.4 | −2.5 | 3 | 0.5 | 1.68 |
| (mg/dl) | (10.6) | (8.1) | (11.5) | | | | 0.205 |

TABLE 6-continued

Sub-group 45 and older
Characteristics, safety, CRP, and lipid profile data on days 0, 30 and 60.

|  | Group means | | | Group differences | | | |
| --- | --- | --- | --- | --- | --- | --- | --- |
|  | D0 N = 14 | D30 N = 14 | D60 N = 14 | D30 − D0 | D60 − D30 | D60 − D0 | F-value P-value |
| CRP | 1.9 (1.9) | 2.5 (2.1) | 1.7 (1.6) | 0.6 | −0.8 | −0.2 | 3.33 0.052 |

Legend:
D0: Baseline values (means with (standard deviations)) prior to the intervention.
D30: Values obtained after 1 month of Immuno Viva intervention.
D60: Values obtained after 1 month of Immuno Viva + Immune Lift intervention.
Statistically significant values are in bold type.

TABLE 7

Sub-group 45 and older
Hematology, immuno chemistry and urine data on days 0, 30 and 60.

|  | Group means | | | Group differences | | | |
| --- | --- | --- | --- | --- | --- | --- | --- |
|  | D0 N = 14 | D30 N = 14 | D60 N = 14 | D30 − D0 | D60 − D30 | D60 − D0 | F-value P-value |
| WBC (k/cmm) | 5.5 (1.6) | 5.5 (1.1) | 5.4 (1.5) | 0 | −0.1 | −0.1 | 0.22 0.808 |
| Neutrophil (%) | 59.6 (5.9) | 59.8 (7.7) | 58.0 (6.9) | 0.2 | −1.8 | −1.6 | 0.97 0.391 |
| Lymphocyte (%) | 27.8 (6.5) | 28.0 (7.9) | 29.4 (6.4) | 0.2 | 1.4 | 1.6 | 1.02 0.376 |
| Monocyte (%) | 9.2 (3.5) | 8.8 (2.3) | 8.7 (2.4) | −0.4 | −0.1 | −0.5 | 0.41 0.666 |
| Eosinophil (%) | 2.8 (1.7) | 2.6 (1.7) | 3.4 (2.0) | −.2 | 0.8 | 0.6 | 4.24 0.026 |
| Basophil (%) | 0.7 (.37) | 0.7 (.30) | 0.5 (.42) | .01 | −0.2 | −0.2 | 2.34 0.176 |
| CD3 | 71.8 (6.9) | 72.3 (6.1) | 71.9 (6.2) | 0.5 | −0.4 | 0.1 | 0.29 0.116 |
| CD4 | 51.1 (7.4) | 51.4 (7.6) | 50.9 (7.7) | 0.3 | −0.5 | −0.2 | 0.24 0.786 |
| CD8 | 20.4 (6.1) | 20.2 (6.5) | 20.0 (5.8) | −0.2 | −0.2 | −0.4 | 0.36 0.704 |
| CD19 | 14.8 (4.8) | 14.7 (4.2) | 14.8 (4.0) | −0.1 | 0.1 | 0 | 0.01 0.990 |
| NK | 12.1 (5.8) | 11.7 (5.1) | 12.2 (4.5) | −0.4 | 0.5 | 0.1 | 0.23 0.795 |
| CD4:CD8 | 2.8 (1.2) | 2.9 (1.3) | 2.8 (1.2) | 0.1 | −0.1 | 0 | 0.39 0.682 |
| Malonyldial. | 2.6 (1.5) | 2.8 (1.5) | 2.7 (1.2) | 0.2 | −0.1 | 0.1 | 0.07 0.933 |
| CD3absol | 234.5 (174) | 244.2 (197) | 240.5 (159) | 9.7 | −3.7 | 6 | 0.23 0.798 |

Legend:
D0: Baseline values (means with (standard deviations)) prior to the intervention.
D30: Values obtained after 1 month of Immuno Viva intervention.
D60: Values obtained after 1 month of Immuno Viva + Immune Lift intervention.
WBC: White Blood Cell Count
NK: Natural Killer Cell
Statistically significant values are in bold type.

Looking at the entire cohort, a statistically significant difference was found in one primary outcome and two secondary outcomes. As was mentioned above, creatinine as a continuous mean level increased significantly over the course of the study but categorically all individual values were within normal safe ranges. Eosinophils increased significantly for the whole population over the course of the study but the proportion of those in normal range remained constant from 27/29 at baseline to 27/29 at day 30 to 26/27 at day 60 (Table 4). Therefore, we can conclude that Immuno-Viva™ and/or Immune Lift™ are safe to take in the amounts given.

Effect of the Composition on Diastolic Blood Pressure

Table 4 shows that diastolic blood pressure dropped significantly from baseline to day 60. While the mechanism of this reduction has not been identified at present, it may be due to endothelial dysfunction associated with free oxygen radicals by affecting nitric oxide levels.

Effect of the composition on LDL cholesterol and eosinophils

Looking at individuals at or above the age of 45 (Tables 6 and 7), two variables were significantly different from their baseline values. Again, eosinophils were higher than baseline values but did not increase the proportion of those who are below or above normal range (See Table 3). LDL cholesterol decreased significantly for the sub-population of individuals at or above the age of 45.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A composition of matter exhibiting diastolic blood pressure lowering activity and LDL cholesterol lowering activity in a human subject, the composition of matter comprising a mixture of cold-pressed botanic seed oils and a mixture of botanic seed flours wherein the mixture of cold-pressed botanic seed oils further comprises a mixture of black cumin seed oil and black raspberry seed oil.

2. The composition of matter of claim 1, wherein the mixture of cold-pressed botanic seed oils further comprises about 50% by weight black cumin seed oil and about 50% by weight black raspberry seed oil.

3. The composition of matter of claim 1, wherein the mixture of botanic seed flours further comprises a mixture of black cumin seed de-fatted flour and black raspberry seed de-fatted flour.

4. The composition of matter of claim 3, wherein the mixture of botanic seed flours further comprises about 50% by weight black cumin seed de-fatted flour and about 50% by weight black raspberry seed de-fatted flour.

* * * * *